United States Patent [19]
Marangoni et al.

[11] Patent Number: 4,772,258
[45] Date of Patent: Sep. 20, 1988

[54] ANGIOPLASTY CATHETER

[75] Inventors: Daniele Marangoni, Milan; Corrado Vassanelli, Verona, both of Italy

[73] Assignee: Kontron Holding A.G., Zurich, Switzerland

[21] Appl. No.: 110,637

[22] Filed: Oct. 15, 1987

Related U.S. Application Data

[63] Continuation of Ser. No. 931,113, Nov. 17, 1986, abandoned.

[30] Foreign Application Priority Data

Nov. 22, 1985 [CH] Switzerland .................. 5235/85

[51] Int. Cl.[4] .............................................. A61B 17/32
[52] U.S. Cl. ........................................ 604/22; 128/305
[58] Field of Search ............ 128/305, 305.1, 751-755; 604/22

[56] References Cited

U.S. PATENT DOCUMENTS

| | | |
|---|---|---|
| 3,592,183 | 7/1971 | Watkins . |
| 4,418,688 | 12/1983 | Loeb ........................ 128/6 |
| 4,445,509 | 5/1984 | Auth ...................... 128/305 |
| 4,631,052 | 12/1986 | Kensey ................ 128/305 X |

FOREIGN PATENT DOCUMENTS

| | | |
|---|---|---|
| 0117519 | 9/1984 | European Pat. Off. . |
| 0147192 | 7/1985 | European Pat. Off. . |
| 2804015 | 8/1979 | Fed. Rep. of Germany ...... 128/305 |
| 3242341 | 5/1984 | Fed. Rep. of Germany . |
| 3340518 | 6/1985 | Fed. Rep. of Germany . |
| 1604860 | 3/1972 | France . |

OTHER PUBLICATIONS

Derwent 84-140968/23 (1984).
Derwent 85-141619/24 (1985).
Derwent 84-220700/36 (1984).

*Primary Examiner*—Michael H. Thaler
*Attorney, Agent, or Firm*—Jon S. Saxe; Bernard S. Leon; George W. Johnston

[57] ABSTRACT

There is disclosed an angioplasty catheter having a drilling head disposed within its distal end. The drilling head having a rotatable drilling tool and means for temporary closing a blood vessel. A shaft position within the interior of the catheter is attached and drives the drilling tool. A pneumatic turbine is connected to the proximal end of the catheter and to the shaft for driving the shaft in drive tool and suctioning material removed by the drive tool.

13 Claims, 2 Drawing Sheets

ANGIOPLASTY CATHETER

This application is a continuation of application Ser. No. 931,113 filed Nov. 17, 1986, now abandoned.

BACKGROUND

1. Field of the Invention

This invention relates to an apparatus for opening constricted or closed blood vessels with a tubular flexible catheter. In particular, the invention relates to an improved angioplasty catheter.

2. Description

Methods of dilating blood vessels by means of catheters are usually referred to as angioplasty. Corresponding catheters are accordingly referred to as angioplasty catheters.

When blood circulation in a patient is interrupted due to an arteriosclerotic lesion or inclusion, frequently an operation can be performed to bypass the interruption. Recently blood vessels have been opened by angioplasty techniques with increasing success. The first angioplasty methods were based on simple dilation of a constriction by means of a balloon catheter which dilated the constriction at relatively high pressure. The disadvantage of this method is that after the balloon catheter is removed the blood vessels partially yield to pressure elastically and subsequently resume their old constricted shape in a relatively short time. The construction returns and the opening of the constriction therefore is not permanent.

In other methods, some of the deposits causing the constriction is removed. This is always necessary should there be an almost complete blockage of the vessel. Both mechanical methods and methods using laser beams have been proposed for this purpose.

DOS No. 32 42 341 describes a catheter, the distal end of which has an expanding head comprising one or more scrapers of resilient material which can be opened by means of a cable attached to a handle disposed at the proximal end of the catheter. The inclusion or deposit can be eliminated with this apparatus by scraping movements. The scrapings from the deposit are carried off by spiral conveyor located inside the catheter. The disadvantage of this apparatus is that the scrapers come into contact with the blood vessel walls and may damage them. There is also a risk that the scrapings may be washed away into the bloodstream if the conveyor inside the catheter does not work effectively. Embolisms, thus, may occur.

The principle of methods using laser beams is to burn a passage through the constriction in the blood vessel. The disadvantage of this method is that the inner surface of the passage burnt through the construction remains relatively rough and therefore tends rapidly to become blocked again.

SUMMARY OF THE INVENTION

The invention concerns a new angioplasty catheter by means of which the disadvantages of the known apparatus of this kind can be obviated.

The inventive catheter is of the kind referred to hereinbefore, but has a drilling head disposed at its distal end, a rotatable drilling tool means for temporarily closing a blood vessel, a shaft in its interior to drive the drilling tool, a drive and connection unit mounted at its proximal end and having drive means for driving the shaft and means for suction-extraction of removed material.

According to an embodiment of the invention the means for temporarily closing the blood vessel are a plurality of vanes which are adapted and configured to open in umbrella fashion and which in the open position close the blood vessel to blood flow in the manner of a non-return valve in dependence on the pressure conditions.

According to another preferred embodiment of the invention, the drilling tool drive shaft is a spiral member which is slidably disposed inside the catheter.

In another preferred embodiment of the invention the drive means comprise a pneumatic turbine which advantageously also is used to produce a negative pressure by means of which the removed material is suction-extracted.

The drilling tool means used according to the invention is preferably a drilling crown, a brush, a sponge, a grinding head or knife.

According to another preferred embodiment, means are provided for introducing an additional catheter (such as a balloon catheter) by which it is possible to close the blood flow in the blood vessel beyond the constriction (working zone) in order to prevent removed particles from being washed away in the bloodstream in a direction away from the catheter.

BRIEF DESCRIPTION OF THE DRAWINGS

Preferred embodiments of the invention will be explained hereinafter with reference to the accompanying drawings wherein.

DETAILED DESCRIPTION OF THE PREFERRED EMODIMENTS

Figure 1:
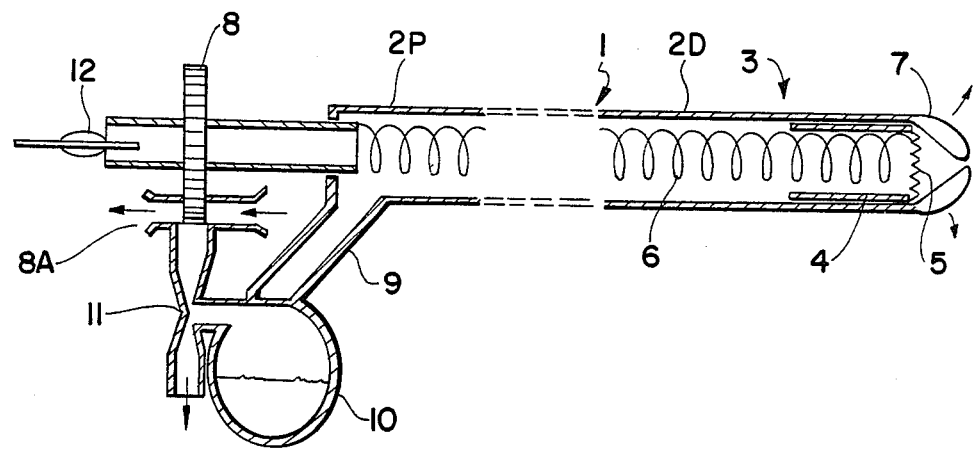
FIG. 1 is a diagram, partly in cross-section, of a catheter according to the invention prior to introduction into a blood vessel.
Figure 2:
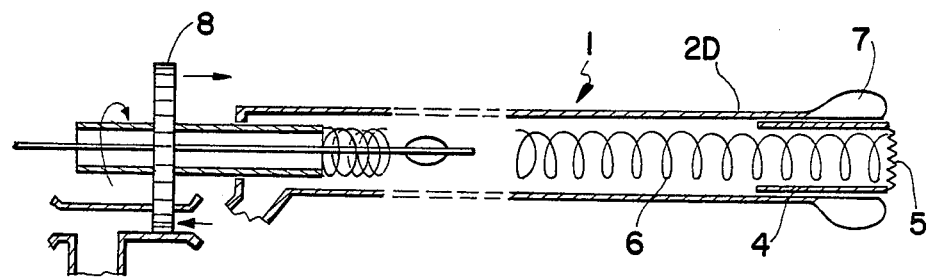
FIG. 2 illustrates the catheter ready for use.

FIG. 1 illustrates an angioplasty catheter 1, the elongate central part of which is shown in broken lines, and which has a distal end 2D and a proximal end 2P. A drilling head 3 is disposed at the distal end 2D and contains a rotatably mounted drilling tool 4. The latter consists basically of a hollow cylindrical member, at one end face of which there are provided sharp-egged teeth 5. A spiral coil 6 has an end fixed to the drilling tool 4 and extends rotatably throughout the length of the catheter 1 and is used to drive the drilling tool 4. The spiral coil 6 is flexible along its longitudinal axis but sufficiently rigid to transmit torque to the drilling tool 4. The drilling head 3 also comprises closure device 7 which covers the end face of the drilling tool 4 in the condition of readiness for introduction as shown in FIG. 1. This device 7 consists of parts in the style of flexible vanes or flaps, which by relative displacement of the drilling head in relation to the catheter can be brought into the open position as shown in FIG. 2. The other (proximal) end of spiral 6 is fixed to an impeller 8 of a pneumatic turbine baving turbine gas inlet 8A at the proximal side 2P of the catheter 1. Turbines of this kind are known to the skilled artisan and need not therefore be described in further detail here.

The proximal end 2P of the catheter 1 also has a connection 9 fluidically communicating with an extraction container 10. The latter is in turn fluidically connected to a vacuum pump 11 which in this embodiment consists of a venturi tube connected to the turbine.

By constructing the drive for the drilling tool 4 in the form of spiral 6, there is an internal cavity in the catheter 1 which is open through which an additional catheter (i.e., a balloon catheter) can be introduced. The function of this balloon catheter 12 will be described hereinafter.

Figure 3:
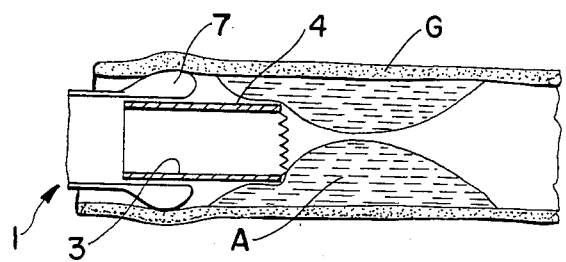
FIG. 3 is a diagram showing a drilling head of the inventive catheter during operation in a blood vessel.
Figure 5:
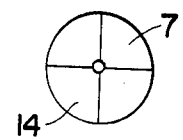
FIG. 5 is a front elevation of the drilling head with a closure device of the inventive catheter in a closed position. i. e. in the condition ready for introduction.
Figure 6:
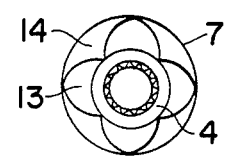
FIG. 6 is a front elevation of the drilling head with the closure device open, i.e. ready for operation.

FIG. 2 shows the inventive angioplasty catheter ready for operation. The drilling tool 4 has been moved forwards relative to distal end 2D of the catheter 1. The closure device thus is opened so that it forms an enlarged diameter radially behind the drilling tool 4. The opening formed with the device 7 will be apparent from comparing the front elevations of FIGS. 5 and 6. FIG. 5 shows the closed position of closure device 7 as shown in FIG. 1. FIG. 6 shows the open condition of closure device 7, the construction of the closure device 7 being apparent from this Figure. It consists of four or more flexible parts 14 in the form of vanes or petals disposed at 90° or less to one another and connected by flexible partitions 13. The device 7 is opened in a radially expanding style of an umbrella or flower. The vanes 14 and the partitions 13 are configured and dimensioned to bear by their outer periphery against the inner wall of the vessel when the closure device is opened. The partitions 13 are flexible. Should the distal pressure at the closure device 7 be equal to or higher than the proximal pressure at the proximal end 2P of the catheter, the device 7 seals tightly against the inner wall of the blood vessel as seen in FIG. 3. Conversely, the partitions 14 fold in or close should there be a distal pressure which is lower than the proximate pressure and, thus, enable blood to flow past and around the device 7.

At the same time as the drilling tool is advanced, the turbine impeller or rotor 8 is moved towards the turbine gas inlet 8A to turn impeller 8, spiral 6 and drilling tool 4.

FIG. 3 shows the drilling head 3 in the operating position. Its purpose is to eliminate deposits A present on the inside of a vessel wall G and constricting the vessel. To this end the catheter is introduced into the vessel until the drilling head 3 is just in front of the constriction. The drilling tool 4 is advanced to open the closure device 7 and the vessel is thus substantially fluidically sealed or closed between the inner wall of blood vessel G and the vanes 14 of closure device 7. As a result, during the subsequent drilling operation none of the removed particles can be washed away along the outside of catheter 1 to the left in the drawing.

The drilling tool 4 is rotated at high speed and advanced further out of closure device 7 and into the deposit. A passage is thus drilled or milled through the deposit. The removed particles of the deposit are extracted through the catheter 11 to its proximal end 2P and into the container 10 by the simultaneous suction effect caused by the turbine and/or vacuum pump 11.

The permanent and continuous application of negative pressure through catheter 1 eliminates any risk of removed particles being washed away to the left in the drawing. However, in order to seal the vessel G in the other direction as well, a balloon catheter 12 can be pushed outwardly through the drilling head 3 and to the other side of the constriction A, where the balloon membrane of the balloon catheter 12 is inflated and thus closes and fluidically seals the vessel G in the other direction at that location. Thus, the particles can not be washed away from the catheter 1 toward the right in the drawings.

Figure 4:
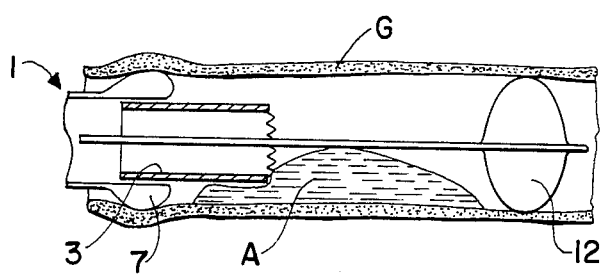
FIG. 4 is an alternative embodiment of FIG. 3 showing the inventive catheter with a balloon catheter.

FIG. 4 also illustrates how sufficient negative pressure which produces the suction for extraction causes some flow of blood past the closure device 7 into the catheter 1 to wash it from the removed particles. The contriction A thus is closed from blood flowing away from the working zone in both directiens of blood vessel G. More particularly, an amount of negative pressure can be applied which will overcome the substantially closed or fluidically sealed condition between the inner wall of blood vessel G and the closure device 7 or balloon catheter 12. respectively. As seen by the arrow in FIG. 4. under this condition with preselected high negative pressure, blood can flow between the closure device 7 and inner wall of blood vessel G and pass through drilling head 3 and the inside of catheter 1.

FIGS. 5 and 6 have been previously discussed. They illustrate closure device 7 in a closed and open position, respectively.

Figure 7:
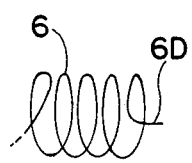
FIGS. 7 to 10 show alternative versions of drilling tools of the inventive catheter.
Figure 9:
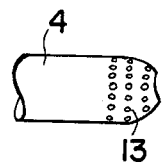

FIGS. 7 and 9 show alternative embodiments of the drilling or cutting tool 4. FIG. 7 is a simple embodiment which has no special drilling tool, the end 6D of the spiral 6 is configured and dimensioned to perform this function instead. To accomplish this, spiral end 6D is bent inwardly in order to avoid damage to the vessel wall. This end 6D can also be configured into a blade and sharpened into a knife.

Figure 8:
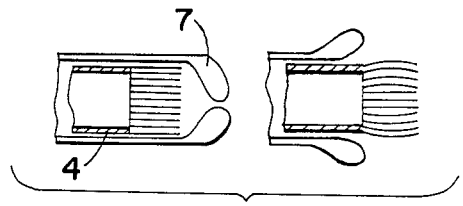

FIG. 8 shows a drilling tool 4 (within and without of closure device 7) in the form of a brush which assumes a widened diameter after being pushed out of the catheter 1 and as a result of the rotation of spiral 6 attached thereto.

Finally, FIG. 9 shows a drilling tool 4 with a sponge-like construction consisting of for example carbon fibers. The removed material from the constriction material is sucked through the apertures 13 to the interior of the catheter tool 4 and through catheter 1.

Figure 10:
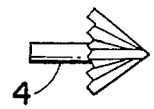

FIG. 10 shows a drilling tool in the form of a drilling crown or grinding head.

The advantage of the angioplasty catheter according to the invention is that with the very high speed provided by the turbine means 8 the drilled passage through the constriction has an extremely smooth surface. This greatly reduces any tendency to the vessel, becoming re-blocked. Also, the risk of removed particles being wash away is eliminated by closing off the working zone around the constriction in one direction by means of the closure device 7 and, if required. in the other direction by means of the balloon catheter 12. At the same time, in this way the catheter is centered in the vessel by closure device 7 and its vanes 14 so that any risk of damaging the vessel wall due to drilling tool 4 being introduced at an angle, for example, is greatly reduced.

While the invention has been described in conjunction with certain embodiments, it is understood that various modifications and changes may be made without departing from the spirit and scope of the invention.

We claim:

1. An apparatus for opening a blood vessel constricted with a deposit such as plaque comprising:
   (a) an elongated, flexible catheter having a proximal end and a distal end;
   (b) a drilling head slidably disposed within the distal end of the catheter and having a rotatable drilling tool means for drilling the deposit from the blood vessel;
   (c) centering and closure means having a proximal side secured to the catheter and a distal side for (i) centering the drilling head in the middle of the blood vessel and (ii) temporarily sealing the blood vessel yet allowing unidirectional blood flow in the direction from the proximal side toward the distal side of the centering and closure means when the pressure on the distal side is less than on the proximal side by a predetermined amount;
   (d) an elongated shaft having a distal end and a proximate end slidably disposed within the catheter, the distal end secured to the drive tool means so as to rotate and advance same through the blood vessel and thereby drill the deposit;
   (e) drive means disposed at the proximal end of the catheter and secured to the proximal end of the shaft for rotating the shaft within the catheter; and
   (f) suction means fluidically communicating with the interior of the catheter for extracting the deposit being drilled by the drilling tool means.

2. The apparatus of claim 1, wherein that the centering and closure means comprise a plurality of flexible vanes which are configured and adapted to open in umbrella fashion and which in the open condition substantially seal the vessel as a non-return valve in dependence on the pressure conditions within the blood vessel.

3. The apparatus of claim 1, wherein the shaft is a spiral member disposed inside the catheter.

4. The apparatus of claim 1, wherein the drive means and suction means comprise a pneumatic turbine which produces a negative pressure by which the deposit is extracted by suction.

5. The apparatus of claim 1, wherein the drilling tool means is a drilling crown.

6. The apparatus of claim 1, wherein the drilling tool means is a brush.

7. The apparatus of claim 1, wherein the drilling tool means is a sponge.

8. The apparatus of claim 1, wherein the drilling tool means is a grinding head.

9. The apparatus of claim 1, wherein the drilling tool means is a knife.

10. The apparatus of claim 1, wherein the drilling tool means is umbrella-shaped with a tip pointing away from the catheter for operation in directions toward and away from the catheter.

11. The apparatus of claim 1, further comprising a balloon catheter having a flexible tube fluidically attached to an expandable and contractable balloon membrane, said balloon catheter being configured and dimension to fit within the angioplasty catheter and advance through the drilling head so as to expand and substantially seal the blood vessel from blood flow.

12. An angioplasty catheter for removing inclusions from blood vessels comprising:
   (a) an elongated, tubular flexible catheter having a proximal end and a distal end;
   (b) a drilling head slidably disposed within the distal end of the catheter and having:
      (i) a rotatable drilling tool means slidably disposed within the distal end of the catheter for rotating and advancing into the inclusion and removing the material of the inclusion from the blood vessel;
   (c) centering and closure means having a proximal side and a distal side and having a plurality of flexible vanes flexibly positioned with its proximal side secured to the distal end of the catheter for (i) advancing radially outwardly, contacting the blood vessel and centering the drilling head in the middle of the blood vessel as the drilling head is slidably advanced from the catheter and (ii) substantially creating a temporary seal between the vanes and the blood vessel yet allowing unidirectional blood flow in the direction from the proximal side toward the distal side of the centering and closure means when the pressure on the distal side is less than on the proximal side by a predetermined amount thereby when sealed temporarily precluding material from the inclusion from escaping into the blood system around the catheter;
   (d) an elongated spiral shaft having a distal end and a proximal end slidably disposed within the catheter, the distal end being fixedly attached to the drilling tool means so as to permit rotation and advancement of same through the blood vessel and drilling of material; and
   (e) pneumatic turbine means secured to the distal end of the catheter and attached to the proximal end of the shaft for rotating and slidably advancing the shaft and drilling head through the catheter and into the inclusion so as to drill the inclusion, said pneumatic turbine means communicating with the interior of the catheter for suctioning and extracting material being drilled by the drill head.

13. The apparatus of claim 12, further comprising a balloon catheter having a flexible tube fluidically attached to an expandable and contractable balloon membrane, said balloon catheter being configured and dimension to fit within the angioplasty catheter and advance through the drilling head so as to expand and substantially seal the blood vessel from blood flow.

* * * * *